United States Patent [19]

Guenther et al.

[11] Patent Number: 5,102,415
[45] Date of Patent: Apr. 7, 1992

[54] APPARATUS FOR REMOVING BLOOD CLOTS FROM ARTERIES AND VEINS

[76] Inventors: Rolf W. Guenther, Bruesseler Ring 73c; Dierk Vorwerk, Neuenhofer Weg 17, both of 5100 Aachen, Fed. Rep. of Germany

[21] Appl. No.: 575,450

[22] Filed: Aug. 30, 1990

[30] Foreign Application Priority Data

Sep. 6, 1989 [DE] Fed. Rep. of Germany ....... 8910603

[51] Int. Cl.⁵ ............................................. A61M 25/00
[52] U.S. Cl. ........................................ 606/159; 604/96
[58] Field of Search .............. 606/127, 159, 200, 198; 604/22, 53, 96, 97, 98, 99, 100, 101, 102, 103, 104, 159, 264, 284

[56] References Cited

U.S. PATENT DOCUMENTS 4,447,227  5/1984  Kotsanis ................................. 604/96
4,611,594  9/1986  Grayhack et al. ................. 606/127
4,669,464  6/1987  Sulepov ................................. 606/198
4,873,978  10/1989  Ginsburg ........................... 606/200
5,011,488  4/1991  Ginsburg ........................... 606/159

Primary Examiner—C. Fred Rosenbaum
Assistant Examiner—William Lewis
Attorney, Agent, or Firm—W. G. Fasse

[57] ABSTRACT

A triple catheter for removing of blood clots from arteries and veins is equipped with an outer catheter (1) that can be inserted into a blood vessel and an inner catheter (5) with an inflatable baloon (6) at its distal end that can be inserted into the outer catheter (1). The inner catheter (5) is surrounded by an intermediate catheter (2) also inserted into the outer catheter (1). The intermediate catheter (2) has a radially expandable distal end receptacle (3) made of an elastic mesh structure of spring wires or plastic monofilaments covered by or embedded in an elastic plastic coating. A very small puncture channel is required for the insertion of such a triple catheter through the wall of a blood vessel.

8 Claims, 2 Drawing Sheets

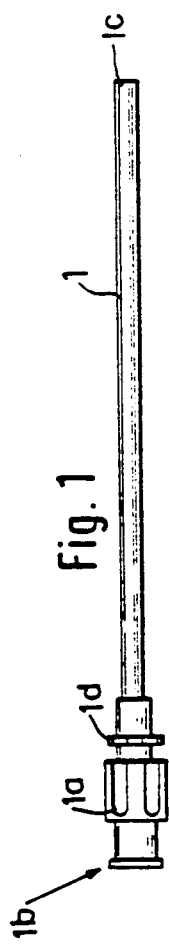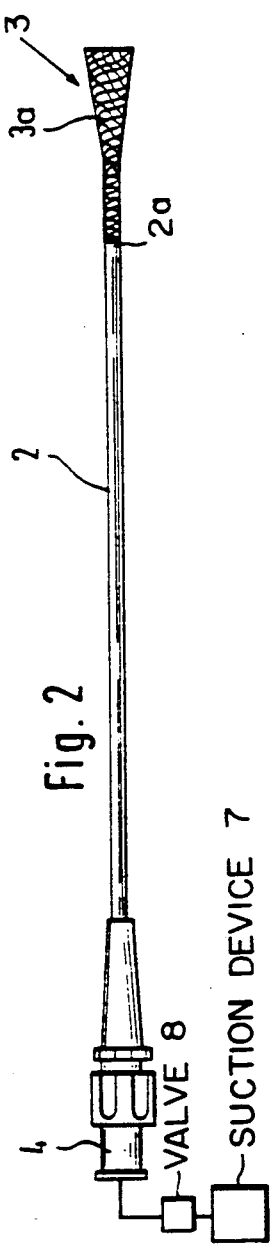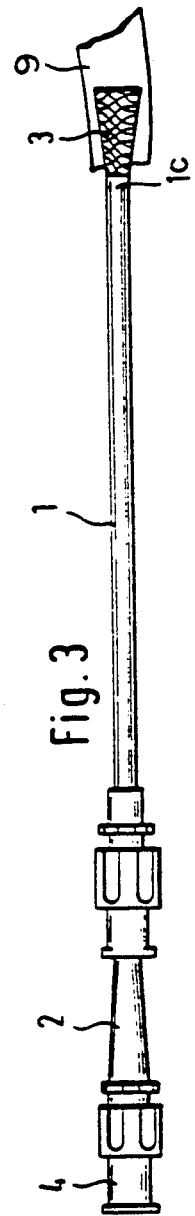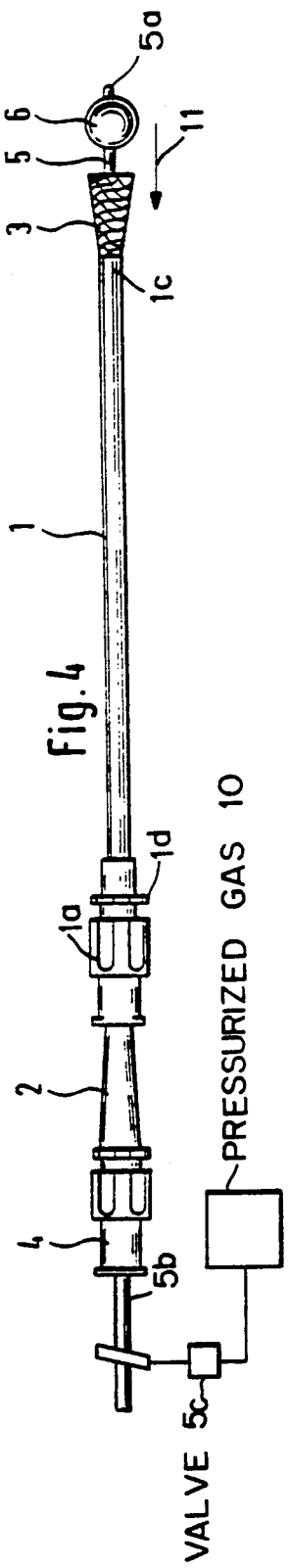

APPARATUS FOR REMOVING BLOOD CLOTS FROM ARTERIES AND VEINS

FIELD OF THE INVENTION

The invention relates to an apparatus for the removal of blood clots from arteries and veins. Such an apparatus includes an outer catheter forming a type of twin lock system or twin sluice system, that can be inserted into a blood vessel. An inner catheter fits through the outer catheter and ends in an inflatable balloon at its distal end. The inner catheter can be introduced into the blood vessel through the outer catheter.

BACKGROUND INFORMATION

Such an inner catheter is known as a Fogarty catheter. The inner catheter is equipped with an inner guide wire. The balloon is in its non-inflated state when the inner catheter is guided through the blood vessel, for example, for pushing the inner catheter tip through a thrombus found in the blood vessel. Thereupon, the balloon is inflated through the inner catheter to the inner diameter of the blood vessel, whereby the balloon is able to push the thrombus ahead of itself as the inner catheter is pulled back out.

Since thrombi and emboli generally extend across the crosssection of a blood vessel, in order to ensure their safe removal by means of a Fogarty catheter, a correspondingly large widening of the catheter insertion point must be made through a surgical cut in the blood vessel after prior surgical exposure under surgery conditions, such as anesthesia and anaemia.

OBJECTS OF THE INVENTION

In view of the foregoing it is the aim of the invention to achieve the following objects singly or in combination:

to construct an apparatus of the type mentioned above in such a way that the safe removal of thrombi and emboli from arteries and veins is assured even through a very small puncture canal;

to provide the distal end of the inner catheter with a gripper type flexible receptacle that can be closed by the inflated balloon after a blood clot or thrombus has been received in the receptacle;

to keep the incision through the patient's skin for the insertion of the outer catheter as small as possible; and to construct the gripper type receptacle so that it will elastically widen or open itself when it emerges from the distal end of the outer catheter.

SUMMARY OF THE INVENTION

The apparatus of the invention has three concentrically arranged catheters, namely an outer catheter for insertion into a blood vessel, an intermediate catheter inside the outer catheter for sluicing a blood clot out, and an inner catheter passing through the intermediate catheter for inserting an inflatable balloon, and a gripper type radially expandable receptacle at the distal end of the intermediate catheter.

According to the invention, the distal end receptacle of the intermediate catheter through which a blood clot is sluiced out widens itself after passing through the outer catheter. The distal end receptacle is preferably moved out of the outer catheter by pulling the outer catheter back by the length of the end receptacle after the intermediate catheter has been introduced and passed through the outer catheter. The receptacle is temporarily and automatically expanded due to its own elasticity and flexibility, so that the outer diameter of the end receptacle conforms to the inner diameter of the blood vessel. This feature permits keeping the cross-section of the puncture or entry point small and unchanged during insertion and extraction. When the end receptacle of the intermediate catheter is in such an expanded state, the blood clot can, with the help of the inflated balloon be pulled into the preferably funnel-shaped expanded distal end receptacle and then pulled to the outside, in a generally known, non-destructive manner. As soon as all of the thrombic material is removed to the outside, the expansion of the receptacle can be contracted again by pulling the intermediate catheter back into the outer catheter. Thus, any blood clots still remaining in the intermediate catheter are removed by pulling the intermediate catheter back out. The present catheter avoids the conventional danger that parts of the blood clot will be sheared off and remain in the blood vessel during the removal of thrombi by conventional apparatus. After the removal of the blood clot, the outer catheter can also be removed from the blood vessel and the closure of the already small puncture or incision point can be achieved through manual compression. Such closure will, as usual, depend on the proper coagulation at the incision point.

According to a further embodiment of the invention, the end receptacle of the intermediate catheter comprises a mesh or weave of spring wires or elastic plastic monofilaments, that is covered by or embedded in an elastic plastic material. The crossing angles of the spring wires or plastic monofilaments are so variable that, through an elastic stretching of the end receptacle beyond its original length, the outer diameter of said end receptacle can be reduced to the inner diameter of the outer catheter. If the end receptacle protrudes out of the distal end of the outer catheter that is placed in the blood vessel, then the crossing angles of the spring wires or plastic monofilaments automatically change and cause an expansion of the diameter of said end receptacle to fit the inner diameter of the blood vessel. If the end receptacle remains partially inside the outer catheter, the portion of said end receptacle that protrudes from the distal end of said outer catheter, takes on a funnel-shape, into the maximum opening cross-section of which the blood clot can be pulled as a whole, by the balloon without the conventional danger that clot edge particles will be sheared off and remain in the blood vessel. The invention avoids leaving any clot portions in the blood vessel. The coating or embedding matrix material of the mesh type receptacle with the expanding and contracting diameter prevents damage to the inner walls of the blood vessel and also prevents the radial leaking of blood clot particles from a blood clot that has been displaced into the end receptacle. It is to be understood, that in the case of a sleeve-shaped coating of the mesh type receptacle, only a thin, very flexible membrane that doesn't significantly effect the expansion capability of the end receptacle, will be used.

According to another embodiment of the invention, the end receptacle of the intermediate catheter has a double-walled construction, at least in the region of its distal opening cross-section. Additionally, the end receptacle is preferably so constructed so it can form a radially expandable and contractable ring space or conical space.

The double-walled construction of the end receptacle is preferably constructed to be inflatable when the receptacle projects out of the distal end of the outer catheter. A pressurized gas for inflating the double wall of the receptacle may be introduced in the same way as is done, for example, for the balloon at the distal end of the inner catheter. A respective duct similar to that of the inner catheter, is used for expanding the double wall of the receptacle to form a funnel-shaped expansion of the end receptacle, the outer diameter of which again conforms to the inner diameter of the blood vessel and the blood clot can also be completely pulled into the end receptacle by means of the inflated balloon.

To simplify the performance of a thromboembolectomy, it is advantageous, according to a feature of the invention, to equip the proximal end of the intermediate catheter with a coupling to which a suction device can be connected.

A further feature of the invention provides that the outer catheter and the intermediate catheter can be fixed relative to each other against an axial movement by a clamping ring attached to the proximal end. During the transfer of a blood clot into the end receptacle, the clamping ring makes sure that the end piece cannot be prematurely pushed back into the outer catheter, whereby its diameter would be reduced before the clot is completely placed within said end receptacle.

BRIEF DESCRIPTION OF THE DRAWINGS

In order that the invention may be clearly understood, it will now be described, by way of example, with reference to the accompanying drawings, wherein:

FIG. 1 shows a side view of an outer catheter;

FIG. 2 shows a side view of an intermediate catheter with an elastic end receptacle according to the invention for removing a blood clot;

FIG. 3 shows an outer catheter with an inserted intermediate clot removal catheter;

FIG. 4 shows an outer catheter with an inserted intermediate catheter and an inserted inner catheter for inflating a balloon;

Figure 5:
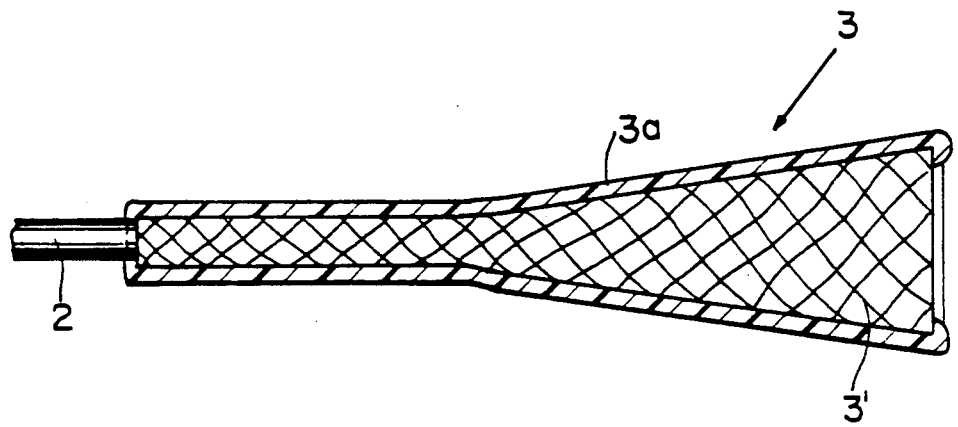
FIG. 5 shows, on an enlarged scale, an axial sectional view through an elastically deformable end receptacle with an elastic coating on its outer surface.

DETAILED DESCRIPTION OF PREFERRED EXAMPLE EMBODIMENTS AND OF THE BEST MODE OF THE INVENTION

FIG. 1 shows an outer catheter 1 constructed in a conventional manner having a Luer coupling 1a at its proximal end 1b and a free distal end 1c. The catheter 1 has a lumen or free crosssection through which an intermediate catheter 2 ca be guided.

FIG. 2 shows the intermediate catheter 2 having a self-expanding end receptacle 3 fixed to the distal end 2a. The end receptacle 3 comprises a tubular mesh structure of spring wires or elastic synthetic filaments forming a tubular spring is covered by a coating or an elastic membrane 3a shown more clearly in FIG. 5. A coupling 4 for the connection of suction means 7 through a control valve 8 is located on the proximal end of the intermediate catheter 2 which serves for extracting or sluicing out a blood clot.

FIG. 3 shows the intermediate catheter 2 of FIG. 2 inserted into the outer catheter 1 of FIG. 1, whereby the receptacle 3 protrudes from the distal end 1c of the outer catheter 1, so that the expanded diameter of the receptacle is larger than the diameter of the outer catheter for fitting against the inner walls of a blood vessel 9.

FIG. 4 shows an inner catheter 5 guided through the intermediate catheter 2. The inner catheter 5 has an inflatable balloon 6 on its distal end 5a. The proximal end 5b of the inner catheter 5 is connectable through a control valve 5c to a source 10 of pressurized gas for inflating the balloon 6.

As mentioned, at least the catheters 1 and 2 are equipped with conventional Luer couplings on their proximal ends. Additionally, a clamping ring 1d is arranged in the area of the Luer coupling between the outer catheter 1 and the intermediate catheter 2, in order to eliminate an unintentional axial displacement of the outer catheter 1 relative to the intermediate catheter 2.

As long as the end receptacle 3 of the intermediate catheter 2 remains inside the outer catheter 1, expansion of said end receptacle 3 is prevented. When the locking ring is released and as soon as the outer catheter 1 is pulled back in the direction toward its proximal end as indicated by the arrow 11 in FIG. 4, the exposed end receptacle 3 expands automatically by reason of the flexibility of its mesh structure which has a spring force stored therein tending to bias the mesh structure radially outwardly, when the mesh structure expansion is not restricted by the wall of the outer catheter 1. This expansion is reversed only when the intermediate catheter 2 with its end receptacle 3 is pulled back into the outer catheter 1, or rather when said outer catheter 1 is pushed over said end receptacle 3. An axially relative displacement between the outer catheter 1 and the intermediate catheter 2 can be repeated as often as desired.

The technical sequence of a thrombus removal with the apparatus of the invention takes place as follows.

First, a percutaneous puncture or incision is made in the artery or vein with a thin calibered needle, according to the conventional Seldinger technique. After threading a customary guide wire into the blood vessel, the puncture canal is widened to the outer diameter of the outer catheter 1 by means of a respective dilator, which is a pointed plastic component and has an inner hollow bore of about 1 mm corresponding to the diameter of the guide wire. The sequence so far is the customary procedure in angiography.

Second, the outer catheter 1 with an inserted or internal dilator is guided into the blood vessel lumen over the already placed guide wire. The internal dilator is necessary for preventing changes in caliber or clearance that could hinder a smooth introduction into the blood vessel. Thereafter, the guide wire and the inserted dilator are removed, while the outer catheter 1 remains in the blood vessel 9. Then, the intermediate catheter 2 with the end receptacle 3 pulled into its small diameter state, is guided into the outer catheter 1. In order to accomplish this, the intermediate catheter 2 is surrounded by a very close lying or tight plastic membrane ending in a distal point or tip. This membrane is perforated along two sides according to known "peel away" wrappings, so that said membrane peels away in two halves through a slight pull applied when the membrane or wrapping is removed after the introduction of the intermediate catheter 2 into the outer catheter 1 has been completed. The two wrapping pieces are pulled out backwardly.

Third, the intermediate catheter 2 is pushed forward in the outer catheter 1 so far distally, that the end receptacle 3 on the distal end of the catheter 2 lies flush with the distal opening of the outer catheter 1. By pulling back the outer catheter 1 in the direction of the arrow 11 relative to the intermediate catheter 2, whereby the end receptacle 3 is exposed and can expand to lie against the wall of the blood vessel 9. After achieving this position, the outer catheter 1 and the intermediate catheter 2 are locked together by the locking ring 1d.

The inner catheter 5 is then introduced into the proximal end of the intermediate catheter 2 and is pushed with the deflated balloon 6 through the thrombus in the blood vessel 9 in the usual manner. The balloon 6 is then inflated outside the thrombus which is thus positioned between the inflated balloon 6 and the distal open end of the receptacle 3 thereby riding on the inner catheter 5. The inner catheter 5 is now pulled back to move the clot into the trumpet-shaped open end of the end receptacle 3. Further pulling of the inner catheter 5 removes the clot to the outside. This procedure can be assisted by means of suction applied by the suction device 7 through the control valve 8.

After complete removal of the thrombus or clot, the outer catheter 1 is pushed distally over the intermediate catheter 2, so that the end receptacle 3 contracts again.

Fourth, the outer catheter 1 and the intermediate catheter 2 are removed together, whereupon the puncture hole or incision can be closed by manual compression.

FIG. 5 shows somewhat enlarged the end receptacle 3 with its mesh structure 3' and its outer elastic coating or membrane 3a made of a suitable synthetic material. The radially outer portions of the mesh structure 3' which surround a funnel or trumpet-shaped opening when the end receptacle 3 is expanded as shown in FIG. 5, may be bonded to the inner surface of the elastic membrane or coating 3a or the filaments of the mesh structure 3' may be directly embedded in the material of the coating or membrane 3a. The fabric or mesh structure 3' may be constructed of spring wires or of synthetic material monofilaments.

Figure 6:
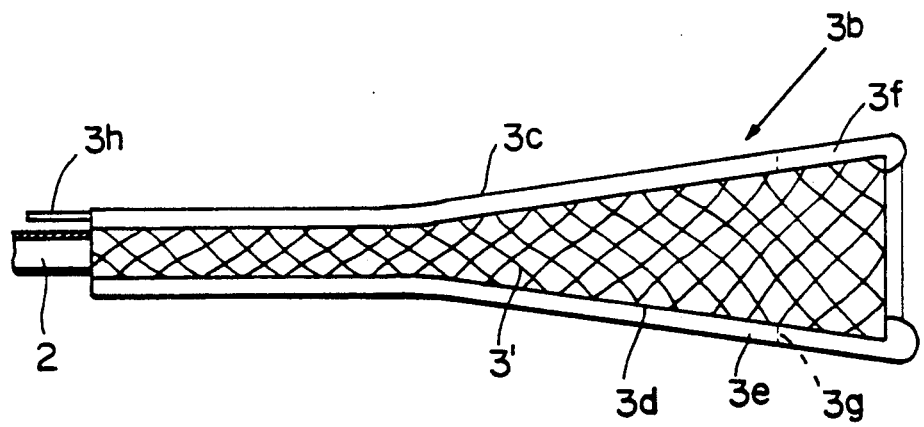
FIG. 6 is a view similar to that of FIG. 5, but showing the end receptacle constructed with a double wall and means for inflating the double wall.

FIG. 6 shows a modified receptacle structure 3b which is enclosed in a double walled hollow jacket having an outer jacket wall 3c and an inner jacket wall 3d. The mesh structure 3' may again be either bonded to or embedded in the inner jacket wall 3d to form the hollow space 3e which is inflatable through a thin tubular member 3h. The tubular member 3h may be attached to the intermediate catheter 2.

The embodiment of FIG. 6 may be further modified by providing the expandable, or rather inflatable, jacket only as a jacket ring member 3f at the distal or open end of the receptacle 3b. In that case, the ring jacket 3f would end at the dashed line 3g and the remainder of the receptacle would be enclosed as shown in FIG. 5. The wires or filaments are sufficiently elastic.

Although the invention has been described with reference to specific example embodiments it will be appreciated that it is intended to cover all modifications and equivalents within the scope of the appended claims.

We claim:

1. An apparatus for removing blood clots from arteries and veins, comprising a first outer catheter, a second intermediate catheter for insertion through said first outer catheter, said second intermediate catheter having a distal tubular end, a third inner catheter for insertion through said second intermediate catheter, clot receptacle means secured to said end of said intermediate catheter, said clot receptacle means comprising an elastically yielding radially expandable tubular spring structure for receiving a blood clot, said tubular spring structure being made of elastical intermeshing elements in the form of spring wires or elastic monofilaments of synthetic materials, said tubular spring structure having a first fixed end diameter fitted and secured to said distal tubular end of said second intermediate catheter and a second diameter that is expandable and contractable along the length of said tubular spring structure when said intermeshing elements assume different angular positions relative to each other inside and outside said first outer catheter, and an inflatable balloon at a distal end of said third inner catheter for pulling a blood clot into said receptacle means when said receptacle means is radially expanded and said balloon is inflated.

2. The apparatus of claim 1, further comprising an elastically yielding jacket enclosing said tubular spring structure.

3. The apparatus of claim 2, wherein said tubular spring structure is embedded in said elastically yielding jacket.

4. The apparatus of claim 1, further comprising a hollow, elastically yielding jacket enclosing at least a portion of said clot receptacle means.

5. The apparatus of claim 4, further comprising means for inflating said hollow jacket.

6. The apparatus of claim 4, wherein said hollow jacket surrounds a distal end of said clot receptacle means to form a ring space into which said balloon fits.

7. The apparatus of claim 1, further comprising means connectable to said second intermediate catheter for applying suction to said intermediate catheter.

8. The apparatus of claim 1, further comprising clamping means arranged at a proximal end of said first and second catheters for locking said first and second catheters to each other to prevent an unintended axial displacement of said first and second catheters relative to each other.

* * * * *